US010426929B2

(12) United States Patent
Burkholz et al.

(10) Patent No.: US 10,426,929 B2
(45) Date of Patent: Oct. 1, 2019

(54) INTEGRATED PERIPHERAL INTRA-VENOUS CATHETER WITH IMPROVED EXTENSION TUBE PORT PROBE ACCESS

(71) Applicant: Becton, Dickinson and Company, Franklin Lakes, NJ (US)

(72) Inventors: Jonathan Karl Burkholz, Salt Lake City, UT (US); Bryan Bihlmaier, Provo, UT (US); Stephen Bornhoft, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/654,467

(22) Filed: Jul. 19, 2017

(65) Prior Publication Data
US 2019/0022357 A1    Jan. 24, 2019

(51) Int. Cl.
*A61M 25/06* (2006.01)
*A61M 25/00* (2006.01)
*A61M 39/10* (2006.01)

(52) U.S. Cl.
CPC .... *A61M 25/0606* (2013.01); *A61M 25/0014* (2013.01); *A61M 25/0029* (2013.01); *A61M 25/0032* (2013.01); *A61M 25/0097* (2013.01); *A61M 39/1055* (2013.01)

(58) Field of Classification Search
CPC ............... A61M 39/45; A61M 39/045; A61M 2039/066; A61M 39/10; A61M 25/0097; A61M 5/0606
See application file for complete search history.

(56) References Cited

U.S. PATENT DOCUMENTS

| | | | | | |
|---|---|---|---|---|---|
| 4,219,912 | A | * | 9/1980 | Adams ............ | A61M 39/02 604/86 |
| 4,871,356 | A | * | 10/1989 | Haindl ............ | A61M 25/00 604/247 |
| 4,874,369 | A | * | 10/1989 | Kulle ............. | A61M 39/04 604/86 |

(Continued)

FOREIGN PATENT DOCUMENTS

WO    WO-2017001656 A1 *   1/2017    ........ A61M 25/0097

*Primary Examiner* — Nathan R Price
*Assistant Examiner* — Mark Alan Igel
(74) *Attorney, Agent, or Firm* — Kirton & McConkie; Craig Metcalf; Kevin Stinger

(57) ABSTRACT

A vascular access device may be an integrated catheter. The vascular access device includes a catheter and catheter adapter having a catheter hub and side port. The contact angle of a probe is greater than 90 degrees. The entrance angle of a probe entering the catheter hub from the side port may be less than 45 degrees. The vascular access device may include a component configured to direct the path of a probe towards the catheter opening. The component may be a protrusion extending into the lumen of the side port, internal fluid passageway, and/or extension tube, or a septum within the catheter hub. The vascular access device includes an access adapter in fluid communication with the side port and permitting insertion of a probe into the catheter through the side port with or without a separate luer adapter. Methods of using a vascular access device are further disclosed.

17 Claims, 20 Drawing Sheets

(56) References Cited

U.S. PATENT DOCUMENTS

| | | | | |
|---|---|---|---|---|
| 4,950,254 A * | 8/1990 | Andersen | A61J 15/0026 604/213 |
| 5,098,405 A * | 3/1992 | Peterson | A61M 39/02 604/247 |
| 5,156,596 A * | 10/1992 | Balbierz | A61M 25/0097 604/164.11 |
| 5,201,717 A * | 4/1993 | Wyatt | A61M 39/04 128/912 |
| 5,267,983 A * | 12/1993 | Oilschlager | A61J 15/0026 285/148.24 |
| 6,158,458 A * | 12/2000 | Ryan | A61J 1/2096 137/515.5 |
| 6,331,176 B1 * | 12/2001 | Becker | A61M 39/06 604/533 |
| 8,070,725 B2 * | 12/2011 | Christensen | A61M 25/0606 604/122 |
| 8,357,121 B2 | 1/2013 | Burkholz | |
| 8,622,967 B2 | 1/2014 | Davis et al. | |
| 8,771,230 B2 * | 7/2014 | White | A61M 25/02 604/174 |
| 8,936,581 B2 | 1/2015 | Bihlmaier | |
| 9,402,975 B2 * | 8/2016 | Shevgoor | A61M 25/0015 |
| 9,517,324 B2 | 12/2016 | Deshpande | |
| D808,013 S * | 1/2018 | Chheda | D24/130 |
| 2002/0177814 A1 * | 11/2002 | Meng | A61M 25/0606 604/164.07 |
| 2005/0043709 A1 * | 2/2005 | Brimhall | A61M 25/0637 604/512 |
| 2007/0093778 A1 * | 4/2007 | Cindrich | A61M 5/158 604/500 |
| 2010/0069781 A1 * | 3/2010 | Johansen | A61B 5/053 600/547 |
| 2013/0237925 A1 * | 9/2013 | Trainer | A61M 25/0097 604/247 |
| 2014/0025039 A1 * | 1/2014 | Rajendran | A61B 17/3401 604/512 |
| 2014/0074031 A1 * | 3/2014 | Bornhoft | A61M 39/10 604/164.01 |
| 2014/0228775 A1 | 8/2014 | Burkholz et al. | |
| 2016/0008582 A1 | 1/2016 | Burkholz et al. | |
| 2016/0220786 A1 | 8/2016 | Mitchell et al. | |
| 2016/0220805 A1 | 8/2016 | Goral et al. | |
| 2016/0325072 A1 | 11/2016 | Shevgoor et al. | |
| 2017/0120001 A1 | 5/2017 | Hyer et al. | |
| 2017/0120010 A1 | 5/2017 | Burkholz et al. | |
| 2017/0120015 A1 | 5/2017 | Burkholz et al. | |
| 2017/0239443 A1 * | 8/2017 | Abitabilo | A61M 25/0097 |
| 2017/0319822 A1 * | 11/2017 | Ang | A61M 25/0097 |
| 2018/0093085 A1 * | 4/2018 | Burkholz | A61M 39/04 |
| 2018/0177993 A1 * | 6/2018 | Fitzgerald | A61M 39/1011 |
| 2018/0184912 A1 * | 7/2018 | Al-Ali | A61B 5/0215 |
| 2018/0200496 A1 * | 7/2018 | Kratzberg | A61M 39/10 |
| 2019/0091462 A1 * | 3/2019 | Bihlmaier | A61M 39/225 |

\* cited by examiner

INTEGRATED PERIPHERAL INTRA-VENOUS CATHETER WITH IMPROVED EXTENSION TUBE PORT PROBE ACCESS

TECHNICAL FIELD

The invention relates to vascular access devices. More specifically, the invention relates to improvements to an integrated catheter system to allow probe access to the fluid path and/or patient's vascular system through an extension tubing side port, and methods for using an integrated catheter system.

BACKGROUND

Peripheral intra-venous catheters (PIVC's) allow rapid access to the vascular system. A probe can be placed in the catheter's fluid path and advanced into the vasculature to allow fluid or medication administration, draw blood, and/or place a sensor for measuring system or patient data. Integrated catheters have gained widespread popularity for a number of reasons. Integrated catheters combine separate components of PIVC's (e.g., catheter device, extension tubing, and needle-free connector) into a single integrated device to reduce the risk of IV catheter failure, blood exposure, and needle sticks for healthcare workers.

Some probes have limitations in their use with integrated catheters. For example, the VELANO VASCULAR™ PIVC blood sampling system does not currently work with integrated catheters such as the Nexiva™ or Nexiva™ Diffusics™ closed IV catheter systems, as it is currently only compatible with non-integrated PIVC's and certain needleless connectors that have an unobstructed fluid path, such as the SmartSite™ and Q-Syte™ needleless connectors. This limitation is associated with the length requirement for a probe to be fed from the luer adapter at the end of the extension tubing, through the extension tubing, catheter adapter, catheter, and beyond the catheter tip into the vascular system using an integrated catheter. Another limitation relates to the probe's inability to follow the fluid path of existing integrated catheters to reach the vascular system without becoming obstructed. In the case of Nexiva™ and other integrated catheters, a probe entering the catheter adapter through the extension tubing may not be able to make the turn into the catheter and beyond while being fed into the system.

Accordingly, it is desirable to obtain a vascular access device, such as an integrated catheter, that facilitates probe access to the device fluid path through the extension tubing side port and into the patient's vascular system without obstruction, and that further allows access near the catheter adapter to reduce the length of the probe needed.

BRIEF SUMMARY OF SOME EXAMPLE EMBODIMENTS

In one aspect, a vascular access device is disclosed. In embodiments, the vascular access device is an integrated catheter.

In embodiments, the vascular access device includes a catheter for insertion into a biological site; and a catheter adapter having a catheter hub and a side port, the catheter hub having a first end operably coupled to the catheter, a second end opposite the first end, and an internal wall defining an internal fluid passageway therebetween, the side port in fluid communication with the internal fluid passageway.

In embodiments, the contact angle of a probe entering the catheter hub from the side port is greater than 90 degrees. In certain embodiments, the contact angle is greater than 90 degrees along the length of the internal fluid passageway and to the first end. In embodiments, the entrance angle of a probe entering the catheter hub from the side port is less than 45 degrees.

In embodiments, the angle between the internal wall and the longitudinal axis of the side port (i.e., a "side port angle") is greater than 90 degrees. In embodiments, the internal wall defines a transition step between a larger diameter portion of the internal fluid passageway proximal to the second end and a smaller diameter portion of the internal fluid passageway at the first end. In some embodiments, a contact angle of a probe entering the catheter hub from the side port, with respect to the transition step, is greater than 90 degrees.

In embodiments, the vascular access device includes a component configured to direct the path of a probe entering the catheter hub from the side port towards the first end. In certain embodiments, the component is a) a protrusion extending into the lumen of the side port, internal fluid passageway, and/or extension tube; b) a septum at least partially within the catheter hub; or c) a combination of protrusion(s) and a septum. In embodiments, the vascular access device includes an access adapter in fluid communication with the side port and permitting insertion of a probe into the catheter through the side port with or without a separate Luer adapter.

In one aspect, a method of using a vascular access device is disclosed, the method including inserting a probe into an extension tube; advancing the probe through the extension tube and into the side port; advancing the probe from the side port through the internal fluid passageway and into the catheter; and advancing the probe through the catheter and into the peripheral vasculature of the subject. In embodiments, the probe maintains a contact angle with the internal wall of greater than 90 degrees along the length of the internal fluid passageway.

BRIEF DESCRIPTION OF THE DRAWINGS

FIG. 15A showing a side port configured with single port near access adapter as a luer adapter; FIG. 15B showing extension tubing configured with a dual port near access adapter as two luer adapters; and FIG. 15C showing extension tubing configured with a dual port near patient access adapter configured as a Luer adapter, and secondary extension tubing.

DETAILED DESCRIPTION

Figure 1:
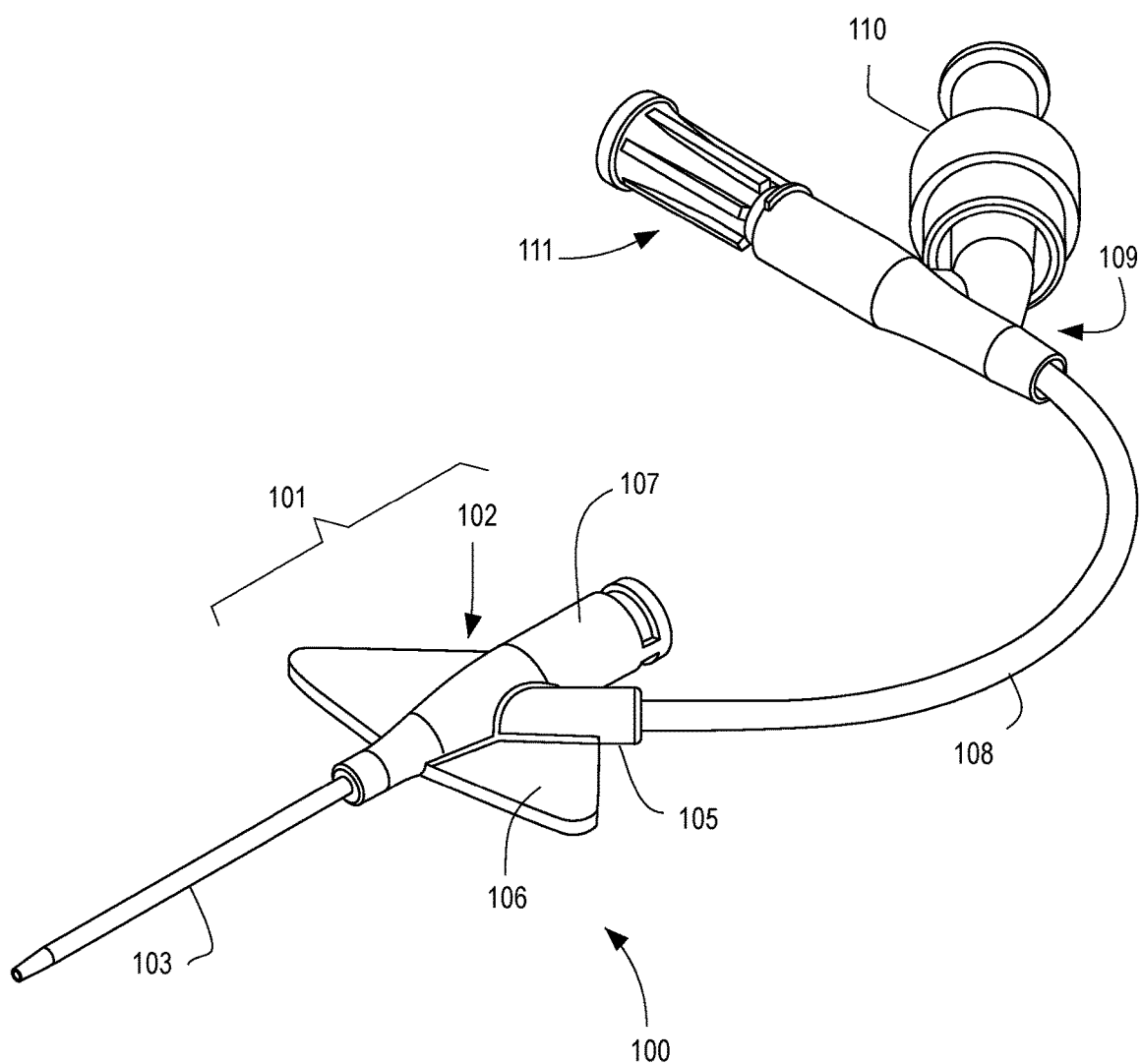
FIG. 1 illustrates an integrated catheter with needleless connector and air vent plug.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein such as, for example, conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE standards) is defined as complying with the currently published standards as of the original filing date of this disclosure concerning the units, measurements, and testing criteria communicated by those standards unless expressly otherwise defined herein. The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof). Where a range of values is provided herein, it is understood to include the upper and lower limits of that range and all values therebetween. For example, a range of 90-120 degrees is understood to mean values of about 90 degrees through about 120 degrees and including all possible values between 90 degrees and 120 degrees.

The invention relates to improvements to an integrated catheter system to allow probe access to the device fluid path and/or patient's vascular system through an extension tubing side port. Conventional probes may be incompatible with existing integrated catheters for a number of reasons. First, the path from a luer adapter, through the extension tubing, catheter adapter, catheter, catheter tip, and beyond the catheter tip into the vascular system is long, creating significant intraluminal frictional resistance and requiring a longer probe that is more difficult to manipulate. Second, the probe makes several turns along this fluid path, increasing the likelihood of encountering obstructions before reaching the vascular system. Accordingly, an integrated catheter system which minimizes sharp turns in the fluid path and/or reduces the distance that the probe must travel will allow probes to be used with integrated catheters through an extension tube side port.

A "vascular access device", as used herein, shall refer to any integrated or non-integrated catheter configured to permit access of a healthcare worker to the vascular system. An "integrated catheter", as used herein, shall refer to a closed intravenous catheter system which integrates individual components usually assembled by the clinician during the insertion of a peripheral IV cannula. For example, as described further herein, an integrated catheter may include a catheter, catheter adapter, side port, and extension tube, and may include additional integrated components. Current designs for integrated catheters such as the BD Nexiva™, BD Pegasus™, and BD Intima II™, include a side port positioned at an angle (typically 45 degrees) to the catheter hub. This causes limitations in the ability to use probes, such as the VELANO VASCULAR™ blood sampling device. The disclosed improvements allow use of these types of probes with an integrated catheter system.

A "probe" or a "vascular probe", as used herein, is a device that can be placed into the catheter system's fluid path and advanced into a patient's vascular system for fluid or medication administration, drawing blood (using combinations of tip opening and/or side holes), and/or placement of a sensor for measuring system or patient data. Sensor are widely placed to monitor a patient's diagnostic information, blood chemistry or other blood parameter, pressure, flow rate, drug ID, microbe detection, or other data of interest. Probes can, for example, be used in combination for intravascular ultrasound, photoacoustic imaging, or near-infrared spectroscopy to evaluate vascular dynamics in near real-time. A probe may thus be a wire, cannula or other tube, or any other extended (hollow or solid) structure capable of passing through the vasculature and (generally) capable of being retracted after use.

In one aspect, a vascular access device is disclosed.

In embodiments, the vascular access device is an integrated catheter.

In embodiments, the vascular access device includes a catheter for insertion into a biological site; and a catheter adapter having a catheter hub and a side port. The catheter hub may have a first end operably coupled to the catheter, a second end opposite the first end, and an internal wall defining an internal fluid passageway therebetween, the side port in fluid communication with the internal fluid passageway. In some embodiments, the vascular access device further includes an extension tube connected to and fluidly coupled with the side port.

As used herein, the term "internal wall" refers to the lumenal wall of the catheter hub approximately opposite the side port. In other words, the internal wall is generally understood to refer to the inner surface of the catheter hub that would first be encountered by an advancing probe, assuming the probe advanced coaxial with the major axis of the side port and the probe is not otherwise deflected by other features as described below. It is understood that the internal wall may be part of the catheter hub or, in some cases, may be formed at least partially by another component lying against the catheter hub. For example, integrated catheters frequently include a catheter wedge that is inserted into the catheter adapter to anchor the catheter to the catheter adapter. This catheter wedge may form and define a portion of the "internal wall" that is first encountered by an advancing probe. Accordingly, in some embodiments, a vascular access device includes a catheter wedge defining at least a portion of the internal wall.

In some embodiments, the contact angle of a probe entering the catheter hub from the side port is greater than 90 degrees.

As used herein, the term "contact angle", when referring to a probe, may refer to the angle between the longitudinal axis of the probe at the tip of the probe, and the internal wall, at the point of contact, as measured from the distal end of the catheter hub major axis. As such, "contact angle" may be understood to capture the angle at the initial moment of contact of the tip of the probe with the internal wall. A contact angle of 90 degrees, which is commonly encountered in existing integrated catheters, identifies a configuration in which the longitudinal axis of the probe nearest the tip of the probe is perpendicular to the internal wall at the point of contact. This approximately 90 degree contact angle is dictated in part by the angle between the side port and catheter hub, as well as the internal architecture of the catheter hub. A contact angle of 180 degrees identifies a configuration in which the longitudinal axis of the probe nearest the tip of the probe is parallel to the internal wall at the point of contact and directed towards the distal end of the catheter hub (i.e., generally towards the lumen of the catheter).

Alternatively, a "side port angle" may be defined in terms of the angle between the internal wall and the longitudinal axis of the side port, without specifically being defined in terms of an advancing probe.

As discussed, one limitation of existing integrated catheters is the risk that an advancing probe may encounter the internal wall at a contact angle of 90 degrees, causing the probe to jam against the internal wall and not advance further into the catheter or, alternatively may encounter the internal wall at a contact angle less than 90 degrees and be directed proximally towards the needle and septum, and away from the lumen of the catheter.

It is also understood that a probe, after making initial contact with the internal wall of the catheter hub, may be deflected in its path with respect to the internal wall such that the contact angle dynamically changes along the length of the internal fluid passageway. Clinical probes are generally made using flexible materials and construction, facilitating some degree of deflection as they are advanced through the system. Accordingly, in some embodiments, the contact angle is greater than 90 degrees along the length of the internal fluid passageway and to the first end. For example, the initial contact angle may be 100 degrees and as the probe is deflected towards the catheter, the contact angle may increase between 100 and 180 degrees until the probe is effectively advancing parallel to the internal wall and may not even be making contact with the internal wall any longer, until it reaches the first end of the catheter hub, or more distal parts of the system.

In some embodiments, the internal wall has a tapered surface.

In some embodiments, the internal wall further defines a transition step between a larger diameter portion of the internal fluid passageway proximal to the second end and a smaller diameter portion of the internal fluid passageway at the first end. In certain embodiments, a contact angle of a probe entering the catheter hub from the side port, with respect to the transition step, is greater than 90 degrees.

A contact angle greater than 90 degrees facilitates advancement of a probe through the catheter adapter and into the catheter. Accordingly, in some embodiments, the contact angle is greater than about 100, 110, 120, 130, 140, 150, 160, or 170 degrees. In a preferred embodiment, the contact angle is greater than about 120 degrees. In some embodiments, the contact angle is about 180 degrees. The ability of a probe to be advanced is dependent on several variables, including the contact angle, material composition of the probe, length of probe that has already been advanced, coefficient of friction with the internal surfaces of the system, lubrication, stiffness of the probe, etc. In some cases, a contact angle of slightly greater than 90 degrees may be sufficient to allow the probe to advance with a gentle applied force. In other cases, such as with a longer probe length, a higher contact angle of 105, 110, 115, or 120 degrees or more may be needed to facilitate advancement.

A variety of adaptations to the disclosed vascular access device may be envisioned for directing the path of the probe through the side port and catheter hub and into the catheter. These adaptations include modifications to the slope, shape, or orientation of the internal wall, and components configured to deflect the path of the probe before the probe encounters the internal wall of the catheter hub.

Figure 6:
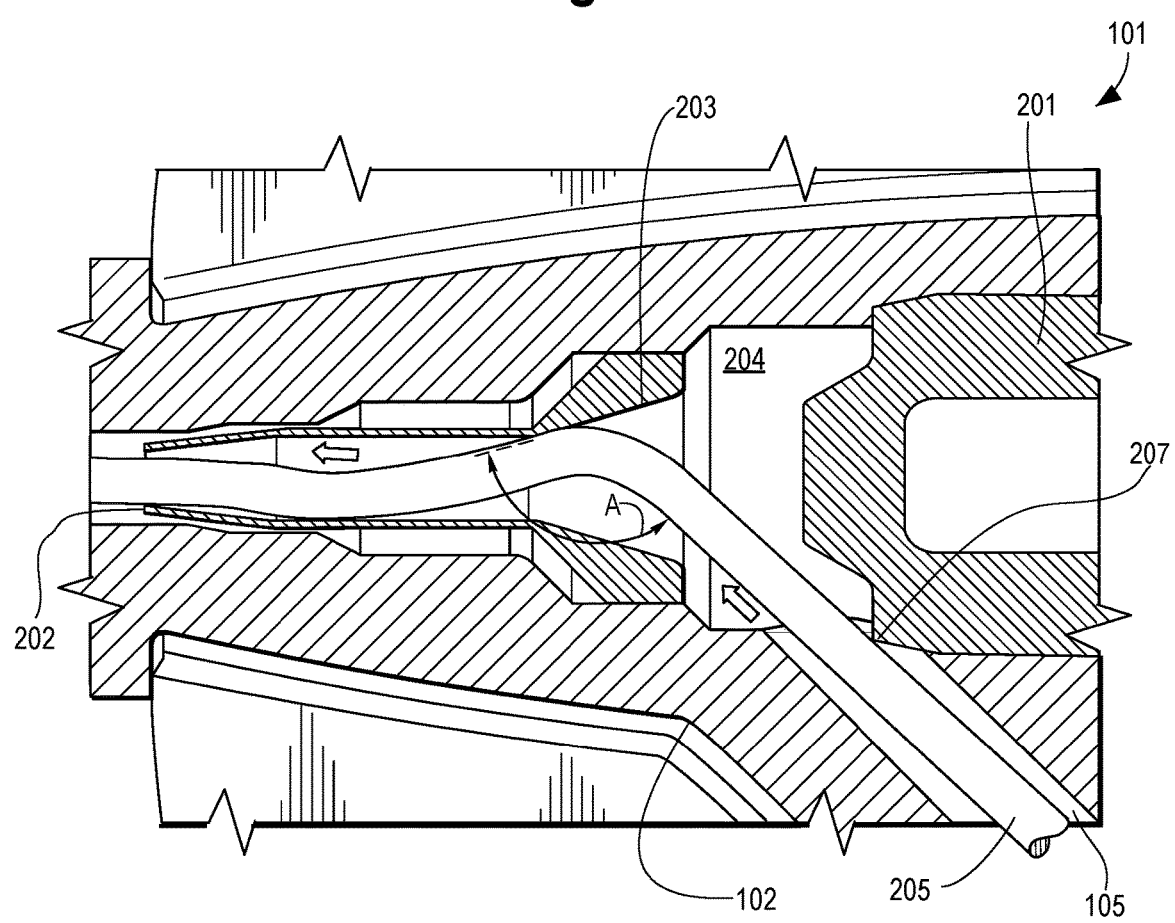
FIG. 6 illustrates a catheter adapter with side port, probe, and septum feature.
Figure 8:
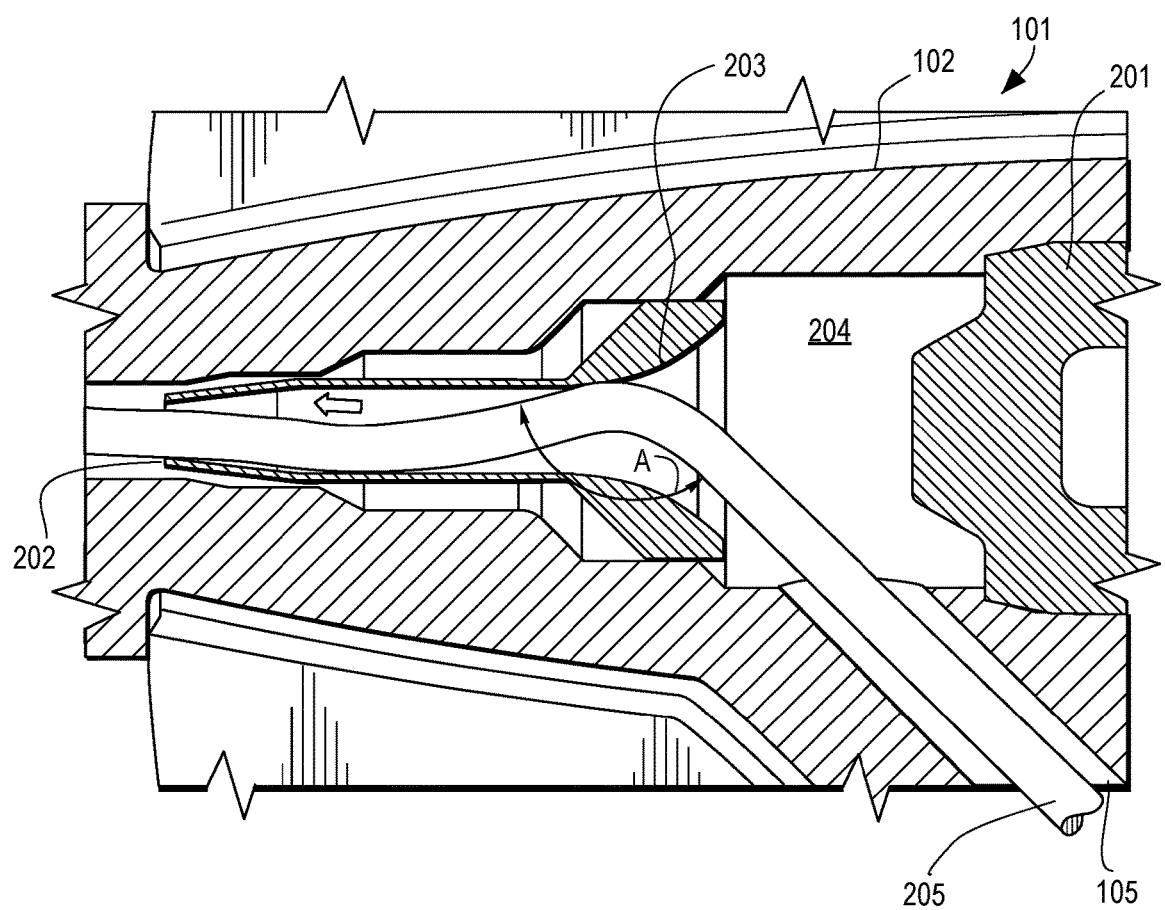
FIG. 8 illustrates a catheter adapter with side port, probe, and convex catheter wedge forming a portion of the internal wall of the catheter hub.

In some embodiments, the slope of the internal wall is decreased, with respect to the major axis of the catheter hub, to increase the contact angle with an advancing probe, as illustrated, for example, in FIGS. 6 and 8. Similarly, the internal wall may have a convex or concave shape such that an advancing probe has a contact angle sufficient to direct the probe to the first end of the catheter hub, as illustrated, for example, in FIGS. 9 and 10.

In one aspect, a vascular access device includes a component configured to direct the path of a probe entering the catheter hub from the side port towards the first end.

In embodiments, the component is a) a protrusion extending into the lumen of the side port, internal fluid passageway, and/or extension tube; b) a septum at least partially within the catheter hub; or c) a combination of a protrusion and a septum.

As used herein, a "protrusion" may refer to any extension, bump, projection, or other modification to the lumenal wall of the side port, internal fluid passageway, and/or extension tube to cause deflection of an advancing probe. A protrusion may be introduced into the aforementioned locations, or alternatively into the catheter hub itself, to increase the contact angle of the probe with the internal wall (i.e., to encourage the probe towards the catheter lumen). A protrusion may be introduced during manufacturing (e.g., molding) of the side port, extension tube, or catheter hub, or may be introduced secondarily using methods known in the art such as heat staking, secondary molding operations, or as a separate component joined to the catheter hub using adhesive, etc.

Integrated catheters commonly include an integrated needle and mechanism for safely retracting and disposing of the needle after use. In these cases, the used needle is generally retracted through a self-sealing septum to minimize fluid leakage. In some embodiments, the septum may be disposed within the catheter adapter at least partially within the path of an advancing probe, such that the advancing probe is deflected by the septum (e.g., towards the first end of the catheter hub).

Other components and adaptations to the side port, internal fluid passageway or other portion of the catheter hub, and/or extension tube may similarly be envisioned that will direct the path of a probe entering the catheter hub from the side port towards the first end, within the scope of the invention.

In some embodiments, a component may so completely direct (i.e., deflect) the path of the probe as it enters the catheter hub that the probe never encounters the internal wall and instead passes directly through the first end and into the catheter.

Other means for directing the path of the probe may also be envisioned which do not necessarily involve a modification to the internal wall or a separate component.

In one aspect, the entrance angle of a probe entering the catheter hub from the side port is less than about 45 degrees. As used herein, the term "entrance angle" may refer to the angle between the advancing probe and the major axis of the catheter hub, as measured from the distal end of the catheter hub. Alternatively, "entrance angle" may refer to the angle between the longitudinal axis of the side port and the major axis of the catheter hub, as measured from the distal end of the catheter hub.

Figure 5:
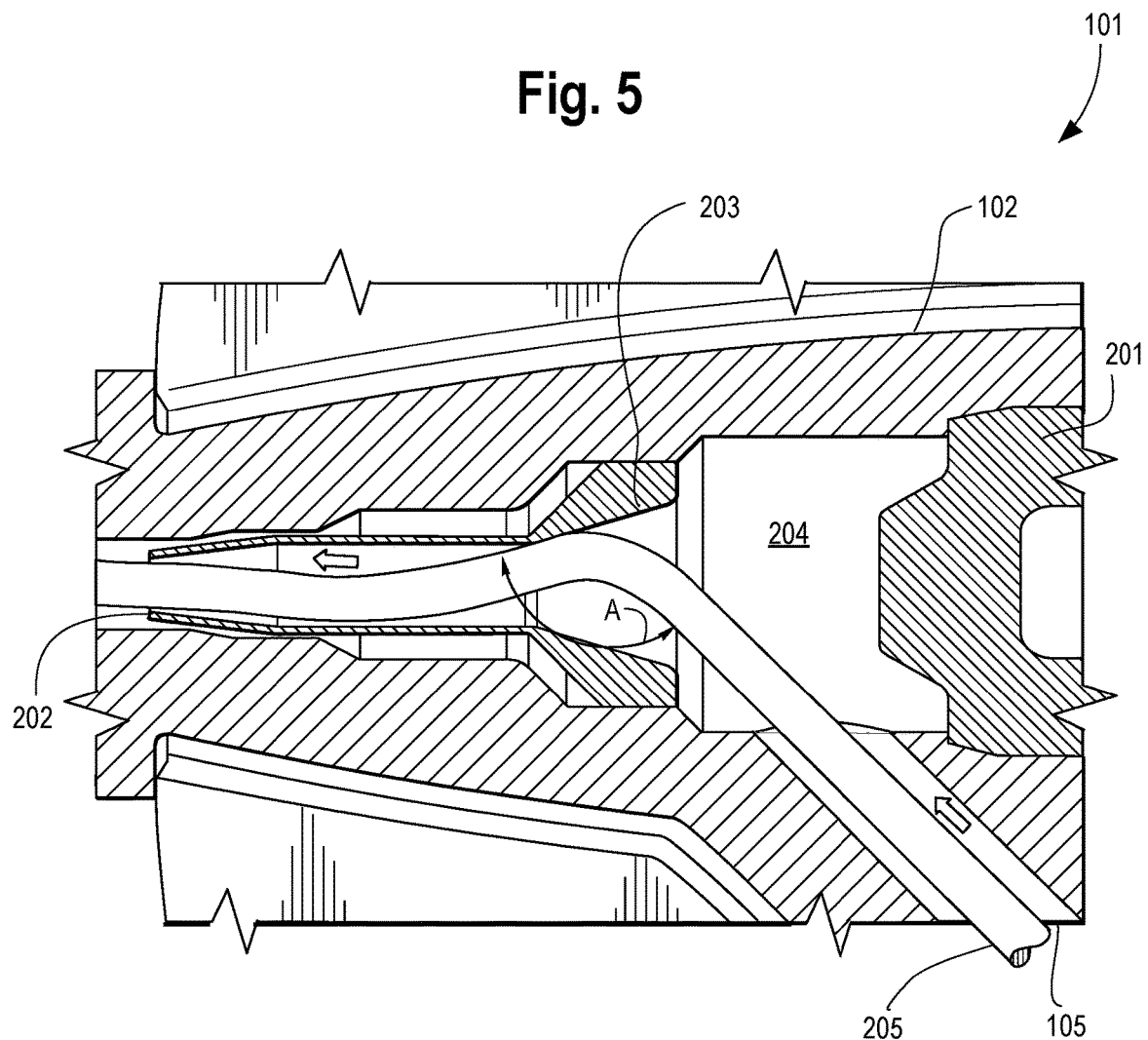
FIG. 5 illustrates a catheter adapter with side port, probe, and extended catheter wedge.
Figure 11:
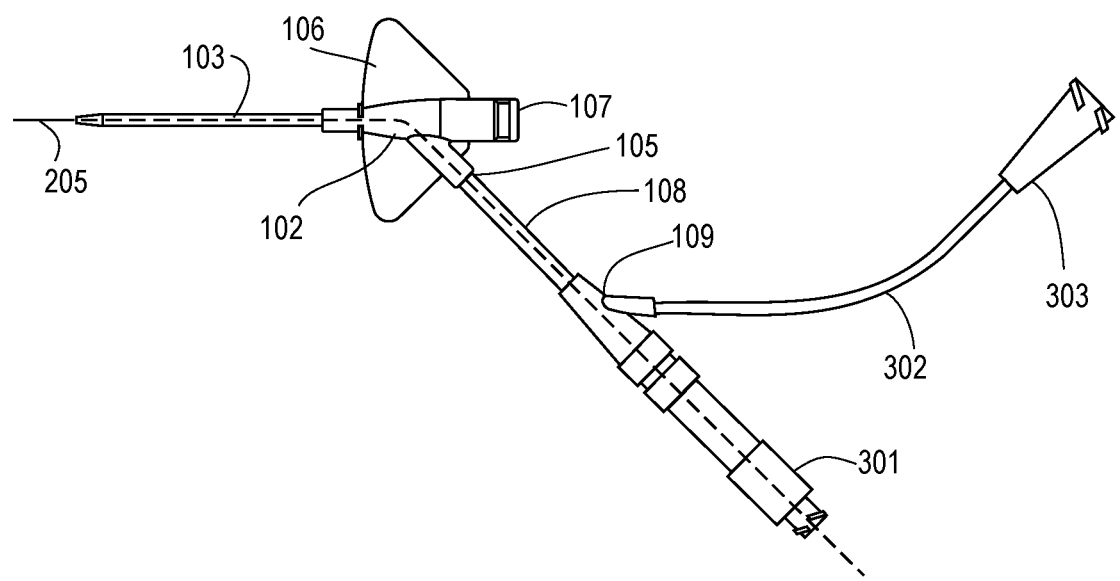
FIG. 11 illustrates an integrated catheter with probe adapter and luer adapter.

In conventional integrated catheters, the entrance angle between the side port and the major axis of the catheter hub is about 45 degrees, as shown for example in FIG. 5. As noted, the entrance angle of the side port influences the path of a probe advancing through the side port and into the catheter hub, thus influencing potentially both the entrance angle of the probe itself and the contact angle of the probe with the internal wall. Accordingly, a shallower (lower) side port entrance angle may be associated with a greater contact angle and facilitate advancement of the probe through the catheter hub, as illustrated in FIG. 11. In some embodiments, the entrance angle of the side port is less than about 45, less than about 40, less than about 35, less than about 30, less than about 25, less than about 20, less than about 15, or less than about 10 degrees.

Various methods for directing the path of the probe and increasing the contact angle are described herein, including, for example, a protrusion in the side port, internal fluid passageway, and/or extension tube. These mechanisms would in some cases be expected to change that entrance angle of a probe entering the catheter hub from the side port. In some embodiments, the entrance angle of a probe entering the catheter hub from the side port is less than about 45, less than about 40, less than about 35, less than about 30, less than about 25, less than about 20, less than about 15, or less than about 10 degrees.

A vascular access device (e.g., integrated catheter) is desired which reduces the distance a probe must travel to reach the vasculature of the patient. Optimally, the vascular access device permits insertion of a probe into an access adapter disposed near the catheter adapter and into the side port, without requiring a separate luer adapter. In this way, the overall length of the path of the probe can be reduced, as compared to conventional integrated catheters, by the probe access adapter being nearer to the catheter adapter than is the luer adapter used to administer or draw fluids via the integrated catheter.

Accordingly, in one aspect, a vascular access device further includes an access adapter in fluid communication with the side port and permitting insertion of a probe into the catheter through the side port with or without a separate luer adapter. Various access adapters may be utilized. In embodiments, the access adapter is selected from the group consisting of a luer adapter, a needle-less connector, a fluid control valve, and a non-luer proprietary access valve designed specifically for probe access. Using the disclosed vascular access devices, the access adapter may be disposed much closer to the catheter adapter than the luer adapter. The use of such a "near-patient" or "near-catheter adapter" access reduces frictional resistance that would otherwise be encountered with a longer probe path. This "near-patient" access may be facilitated by, and in some cases, may require, a contact angle greater than 90 degrees, as described previously.

It is further understood that one or any combination of the features described above may be utilized to facilitate passage of a probe through the side port of a catheter adapter and into the catheter. For example, in some embodiments, a vascular access device includes a) a protrusion extending into the lumen of the side port, internal fluid passageway, and/or extension tube; b) a septum at least partially within the catheter hub; c) an extended, concave, or convex internal wall; and/or d) a side port entrance angle of less than 45 degrees.

In one aspect, methods of using a vascular access device are disclosed. In embodiments, the vascular access device is an integrated catheter.

In embodiments, the method includes inserting a probe into an extension tube of the vascular access device; advancing the probe through the extension tube and into the side port; advancing the probe from the side port through the internal fluid passageway and into the catheter; and advancing the probe through the catheter and into the peripheral vasculature of the subject.

In some embodiments, the probe maintains a contact angle with the internal wall of greater than 90 degrees along the length of the internal fluid passageway.

In some embodiments, the probe is passed through an access adapter before being inserted into the extension tube, the access adapter in fluid communication with the extension tube and permitting insertion of the probe into the catheter through the side port with or without a separate luer adapter.

In other embodiments, the probe is passed through an access adapter and directly into the side port (not requiring an extension tube), with or without a separate luer adapter.

FIG. 1 illustrates an embodiment of integrated catheter 100 with needleless connector 110 and air vent plug 111. As shown, integrated catheter 100 includes a catheter adapter 101 with catheter hub 102, catheter 103, side port 105, two radial wings 106, needle housing 107, and integrated extension tubing 108. Extension tubing 108 is fluidly connected to side port 105 and terminates in y-adapter 109, leading to Q-Syte™ needleless connector 110 and air vent plug 111.

Figure 2:
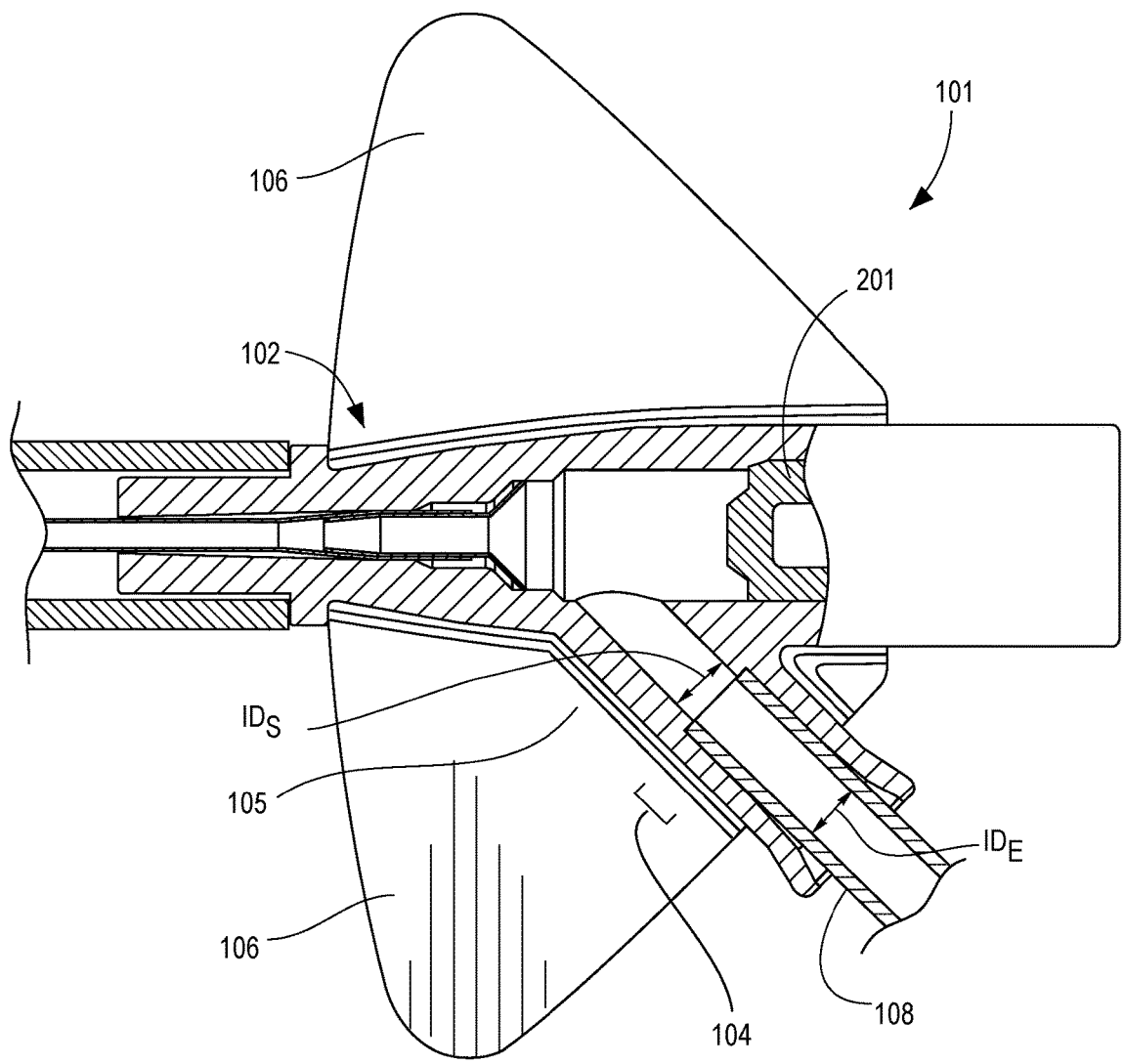
FIG. 2 illustrates a catheter adapter with side port.

FIG. 2 illustrates another embodiment of catheter adapter 101 with catheter hub 102, side port 105, radial wings 106, and extension tubing 108. As shown, side port 105 is joined with extension tubing 108 at bond pocket 104. As a probe advances distally through an integrated catheter, the inner diameter of downstream (more distal) passageways in the path of the probe generally increases, particularly at joints. Thus, $ID_S$ (inner diameter of side port) is generally greater than $ID_E$. (inner diameter of extension tube) to facilitate advancement of the probe. FIG. 2 further shows the inner face of septum 201 associated with needle retraction.

Figure 3:
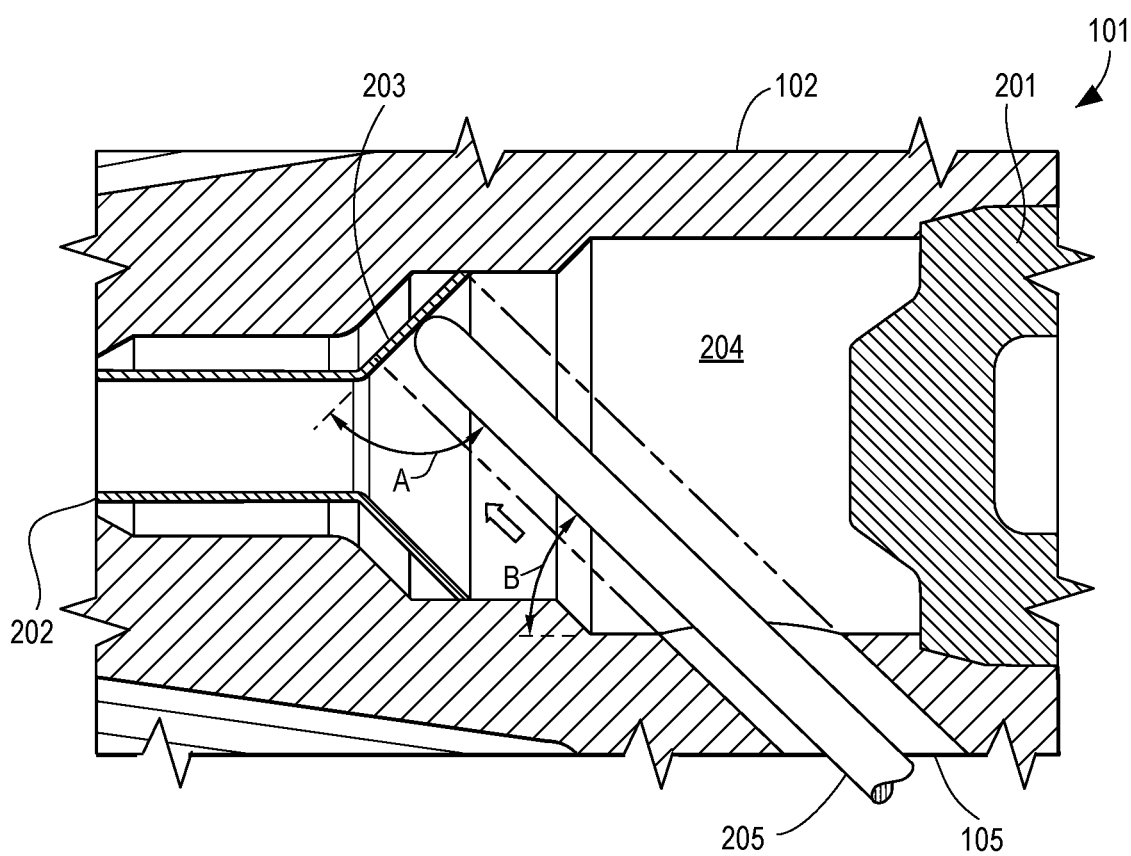
FIG. 3 illustrates a catheter adapter with side port and probe.

FIG. 3 illustrates another embodiment of catheter adapter 101 including catheter hub 102 and side port 105. The inner face of septum 201 is shown to the right side of catheter hub 102 forming a seal to prevent blood or other fluid leakage after needle retraction. Catheter 103 (not shown) is anchored in catheter adapter 101 with catheter wedge 202. Internal wall 203 is shown within catheter hub 102 defining internal fluid passageway 204 between a first end of catheter hub 102 operably coupled to the catheter and a second end of catheter hub 102 opposite the first end. Probe 205 has advanced through side port 105 and is making contact with internal wall 203. Catheter wedge 202 defines a portion of internal wall 203, including the portion contacted by probe 205 in this embodiment. The contact angle A of probe 205 with internal wall 203 is about 90 degrees and the entrance angle B of probe 205 is about 45 degrees. Accordingly, probe 205 contacts internal wall 203 and will not readily advance into catheter 103.

Figure 4:
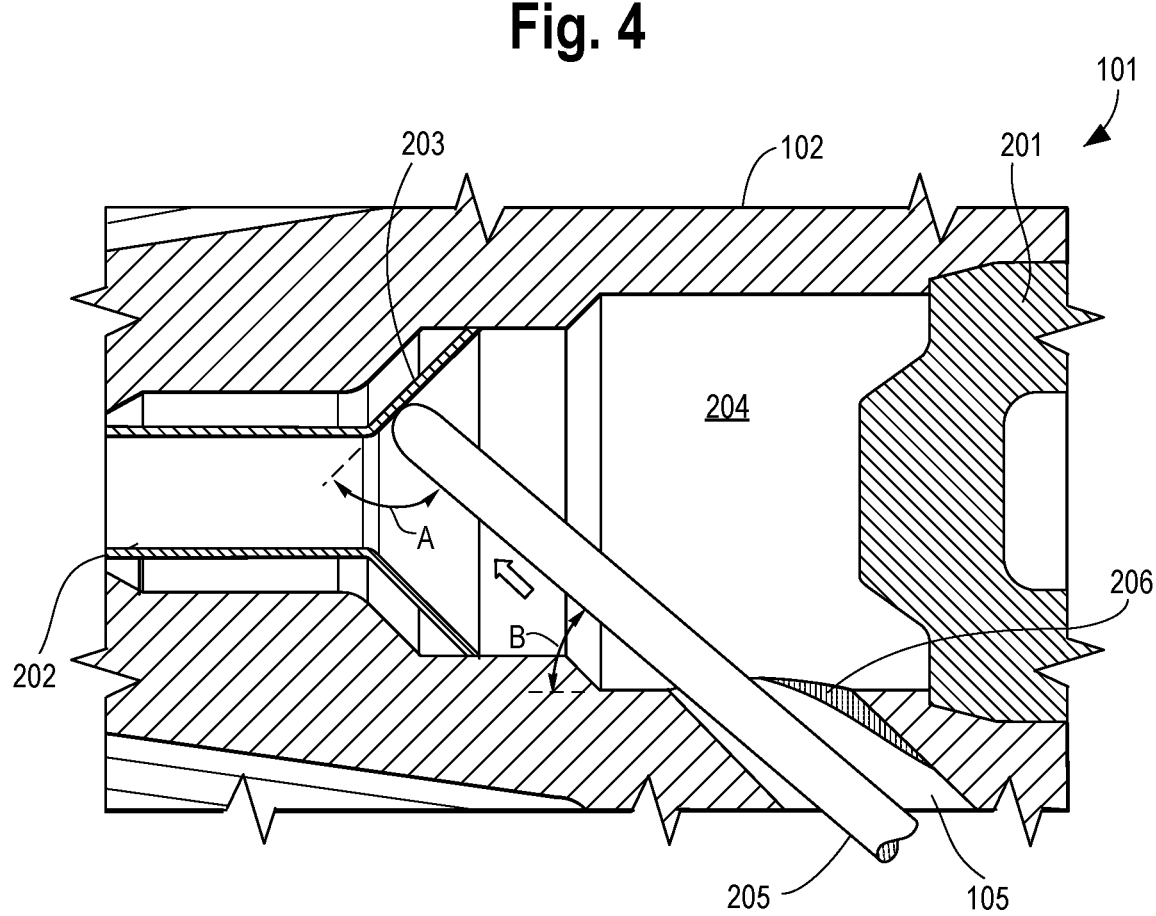
FIG. 4 illustrates a catheter adapter with side port, probe, and protrusion inside the side port.

FIG. 4 illustrates another embodiment of catheter adapter 101 including catheter hub 102 and side port 105, with catheter wedge 202 defining a portion of internal wall 203. Probe 205 encounters protrusion 206 (within side port 105) and is deflected towards the first end of catheter hub 102 (i.e., deflected in a distal direction). As shown, contact angle A of probe 205 is accordingly increased (greater than 90 degrees), and entrance angle B of probe 205 is accordingly decreased (less than 45 degrees) as compared to the embodiment of FIG. 3, encouraging the path of the probe towards catheter 103 (i.e., to the left in FIG. 4). In the illustrated embodiment, probe 205 may advance into catheter 103 after contacting internal wall 203 (for example, with slight additional force).

FIG. 5 illustrates another embodiment of catheter adapter 101 including catheter hub 102, catheter wedge 202, and side port 105, with catheter wedge 202 defining a portion of internal wall 203. In this embodiment, the slope of internal wall 203 is decreased relative to the major axis of the catheter hub (i.e., an "extended" internal wall) to increase the contact angle A with probe 205. Accordingly, probe 205 is shown contacting internal wall 203 and being directed towards catheter 103 (not shown), facilitated by the decrease in slope of internal wall 203.

FIG. 6 illustrates another embodiment of catheter adapter 101 including catheter hub 102, catheter wedge 202, and side port 105, with catheter wedge 202 defining a portion of internal wall 203. In this embodiment, septum 201 is displaced distally within catheter hub 102 relative to its position in FIGS. 3, 4, and 5. Probe 205 advances into side port 105 and contacts septum 201, which deflects probe 205 towards the first end of catheter hub 102 and towards catheter 103 (i.e., to the left in FIG. 6). The point of septum-probe contact 207 is further shown.

Figure 7:
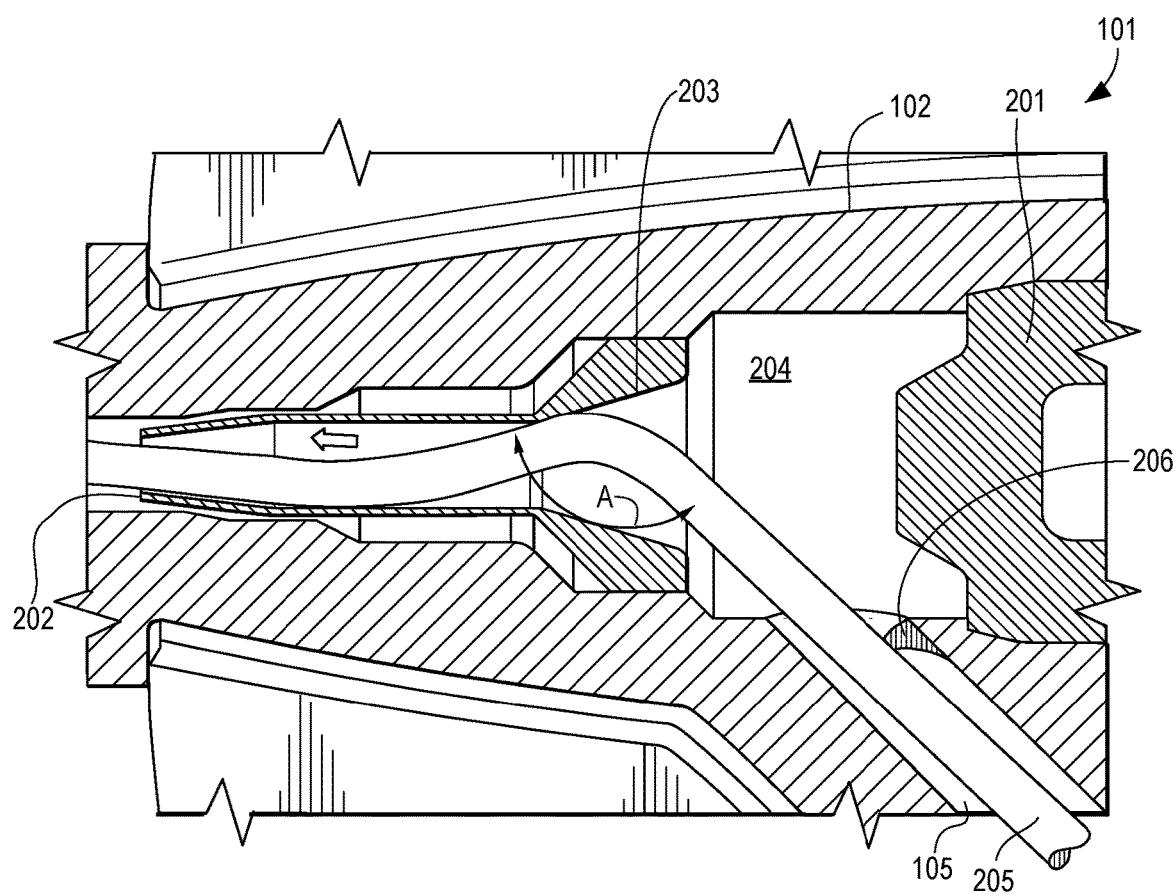
FIG. 7 illustrates a catheter adapter with side port, probe, extended catheter wedge, and protrusion inside the side port.

FIG. 7 illustrates another embodiment of catheter adapter 101 including catheter hub 102, catheter wedge 202, and side port 105, with catheter wedge 202 defining a portion of internal wall 203. In this embodiment, protrusion 206 is shown extending into the lumen of side port 105, deflecting probe 205 toward first end of catheter hub 102 (i.e., to the left in FIG. 7). In addition, the slope of internal wall 203 is again decreased relative to the major axis of the catheter hub (i.e., forming an extended internal wall). The combination of these features increases the contact angle A with probe 205 (greater than 90 degrees). Accordingly, probe 205 is shown first being deflected by protrusion 206 then contacting internal wall 203 and being directed further towards catheter 103 (i.e., to the left in FIG. 7).

FIG. 8 illustrates another embodiment of catheter adapter 101 including catheter hub 102, catheter wedge 202, and side port 105, with catheter wedge 202 defining a portion of internal wall 203. In this embodiment, internal wall 203 has a convex surface at the point of contact with probe 205 that helps direct probe 205 towards the first end of catheter hub 102 and towards catheter 103 (i.e., to the left of FIG. 8).

Figure 9:
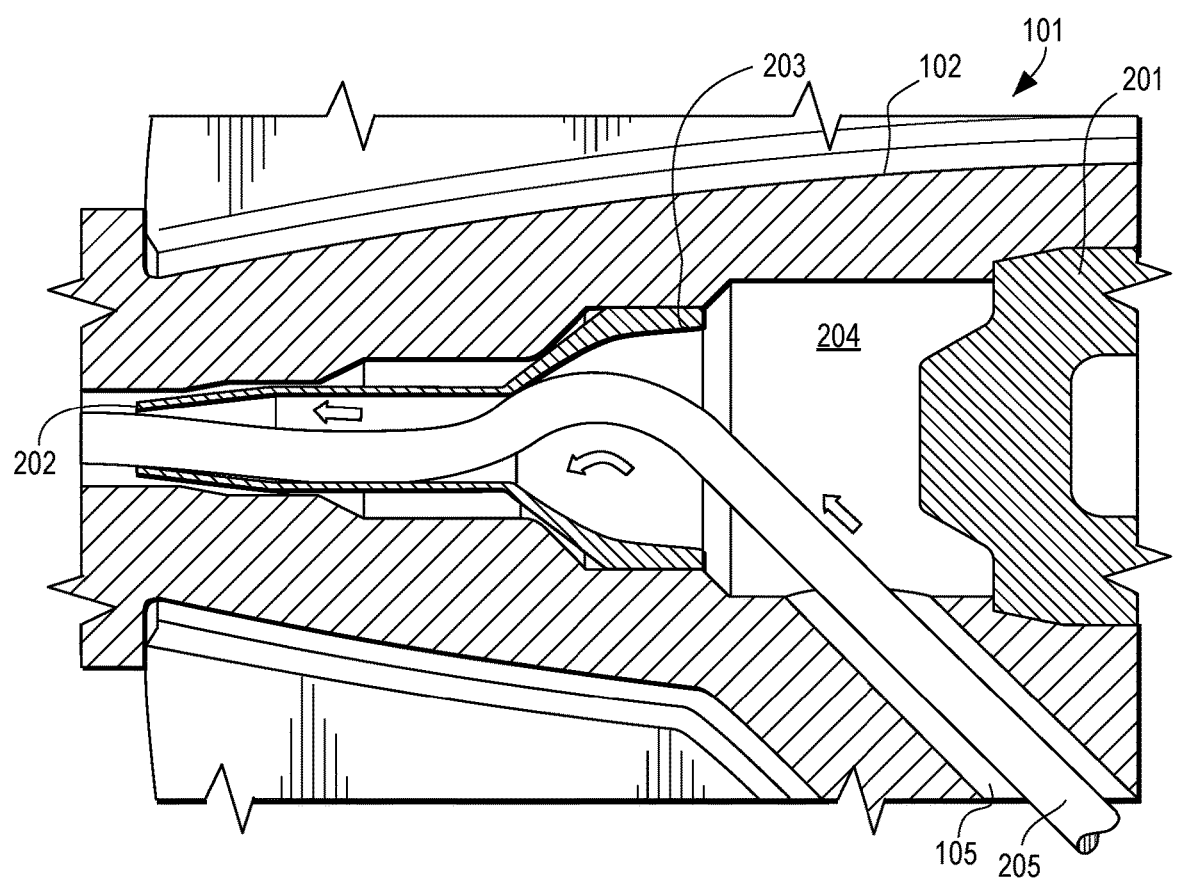
FIG. 9 illustrates a catheter adapter with side port, probe, and concave catheter wedge forming a portion of the internal wall of the catheter hub.

FIG. 9 illustrates another embodiment of catheter adapter 101 including catheter hub 102, catheter wedge 202, and side port 105, with catheter wedge 202 defining a portion of internal wall 203. In this embodiment, internal wall 203 has a concave surface at the point of contact with probe 205 that helps direct probe 205 towards the first end of catheter hub 102 and towards catheter 103 (i.e., to the left of FIG. 9).

Figure 10:
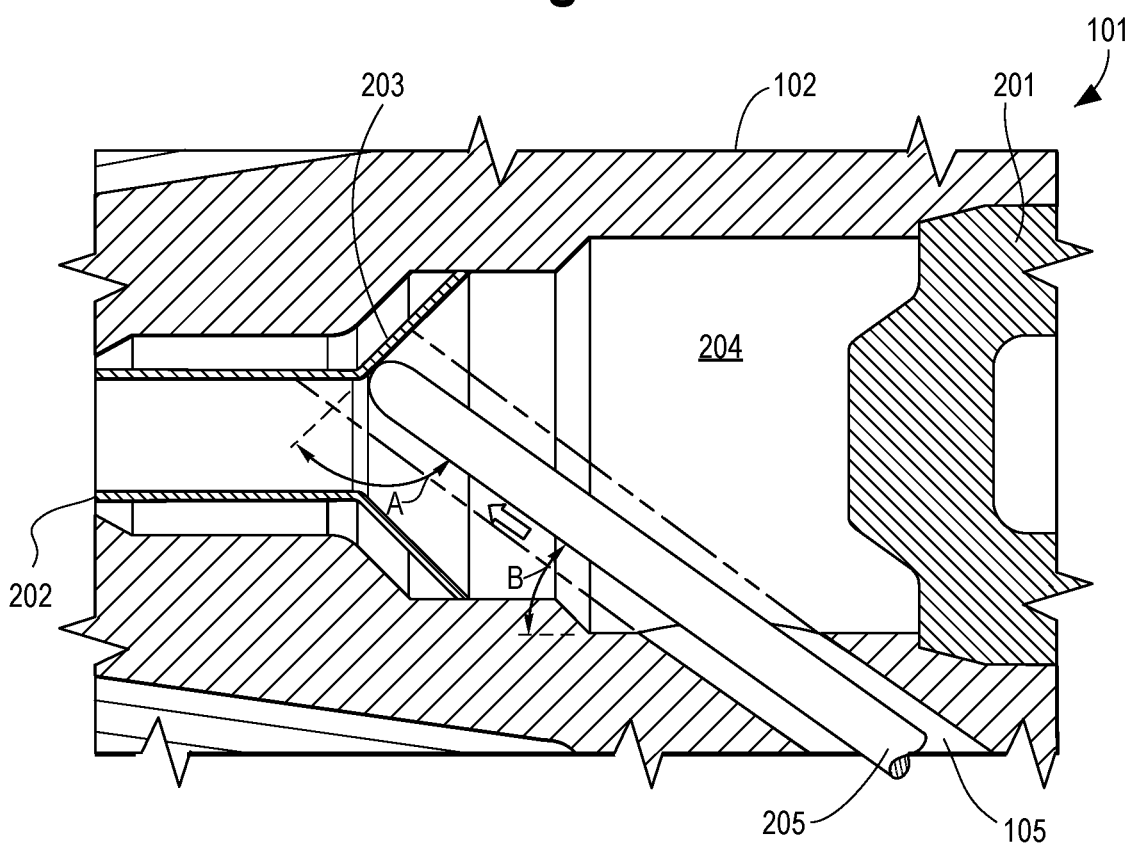
FIG. 10 illustrates a catheter adapter with side port having a shallow entrance angle with respect to the catheter hub.

FIG. 10 illustrates another embodiment of catheter adapter 101 including catheter hub 102, catheter wedge 202, and side port 105, with catheter wedge 202 defining a portion of internal wall 203. In this embodiment, internal wall 203 has a slope similar to that shown in FIGS. 3 and 4, but side port 105 has been tilted so that the entrance angle of side port 105 is reduced. Accordingly, entrance angle B of probe 205 is reduced (less than 45 degrees) and contact angle A of probe 205 is increased (greater than 90 degrees), encouraging probe 205 towards catheter 103 (i.e., to the left in FIG. 10).

It is contemplated that any of the aforementioned features for directing probe 205 into catheter 103, including any combination thereof, may be present in a given vascular access device or integrated catheter.

FIGS. 11-14 illustrate various configurations of near patient access adapters, for use with the disclosed vascular access devices.

FIG. 11 illustrates an integrated catheter with catheter hub 102, catheter 103, side port 105, wings 106, needle housing 107, and extension tubing 108. In this configuration, extension tubing 108 terminates in a dual port y-adapter 109, with probe adapter 301 and luer adapter 303. As shown, probe adapter 301 is configured for near patient access, allowing insertion of probe 205 into extension tubing 108 and through side port 105, catheter hub 102, and catheter 103, as shown. While shown with a luer adapter, the integrated adapter could also be configured without a luer adapter for this access.

Figure 12:
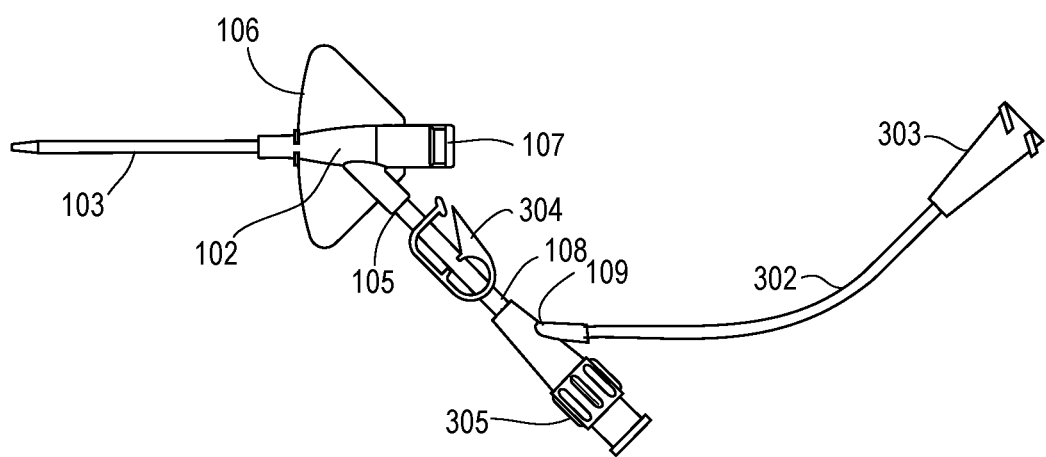
FIG. 12 illustrates an integrated catheter with needle-less connector and luer adapter.

FIG. 12 illustrates an integrated catheter with catheter hub 102, catheter 103, side port 105, wings 106, needle housing 107, extension tubing 108, and clamp 304. In this configuration, extension tubing 108 terminates in a dual port y-adapter 109, with removable needleless connector 305 and secondary extension tubing 302 leading to luer adapter 303.

Figure 13:
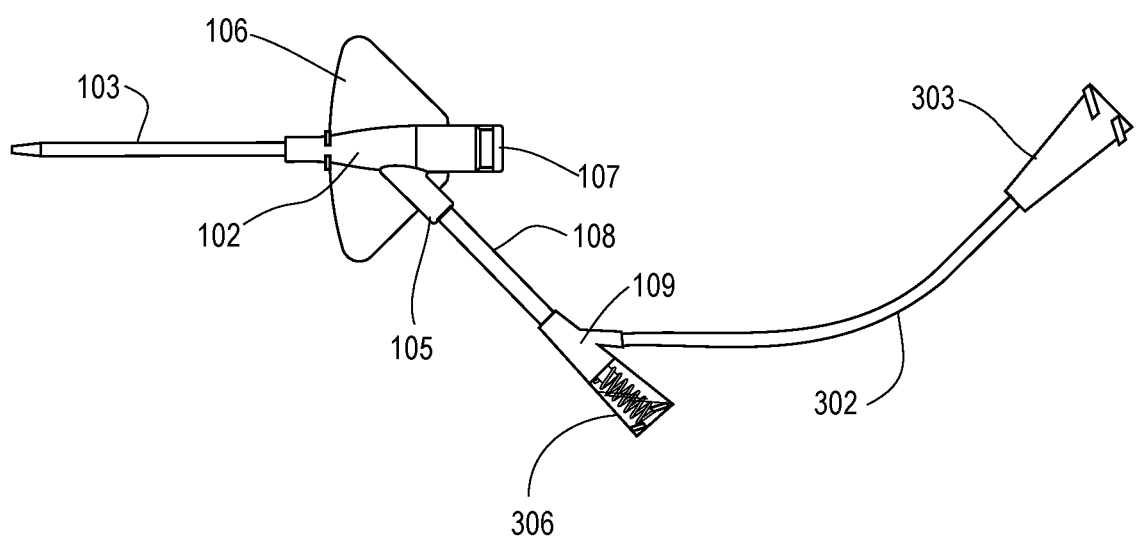
FIG. 13 illustrates an integrated catheter with fluid control adapter and luer adapter.

FIG. 13 illustrates an integrated catheter with catheter hub 102, catheter 103, side port 105, wings 106, needle housing 107, and extension tubing 108. In this configuration, extension tubing 108 terminates in a dual port y-adapter 109, with fluid control adapter 306 and secondary extension tubing 302 leading to luer adapter 303.

Figure 14:
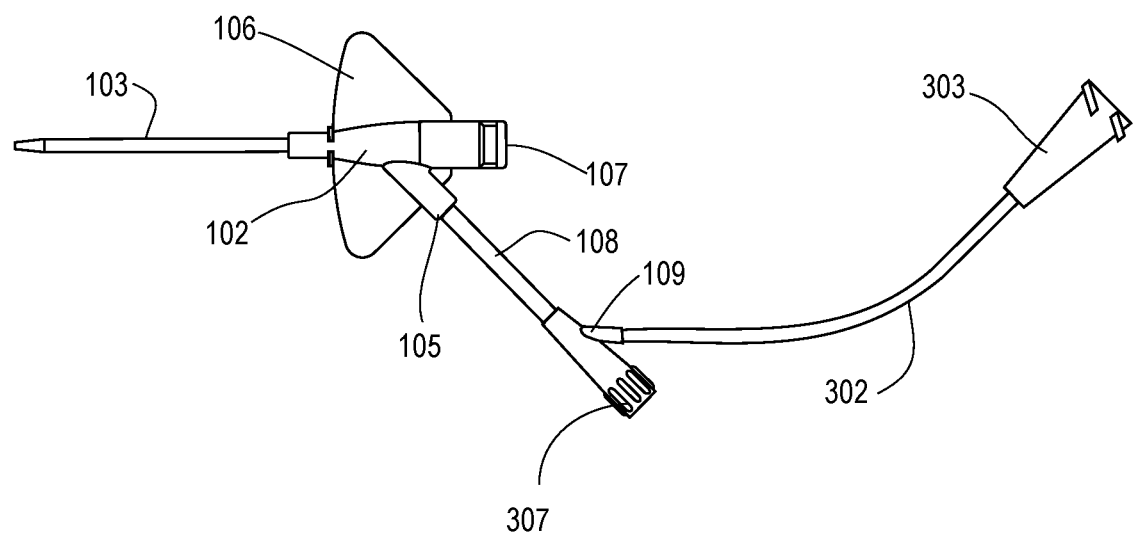
FIG. 14 illustrates an integrated catheter with non-luer septum adapter and luer adapter.

FIG. 14 illustrates an integrated catheter with catheter hub 102, catheter 103, side port 105, wings 106, needle housing 107, and extension tubing 108. In this configuration, extension tubing 108 terminates in a dual port y-adapter 109, with non-luer septum adapter 307 and secondary extension tubing 302 leading to luer adapter 303.

It is understood that the disclosed vascular access devices (e.g., integrated catheters) may be used with any number of other configurations for near patient access.

Figure 15A:
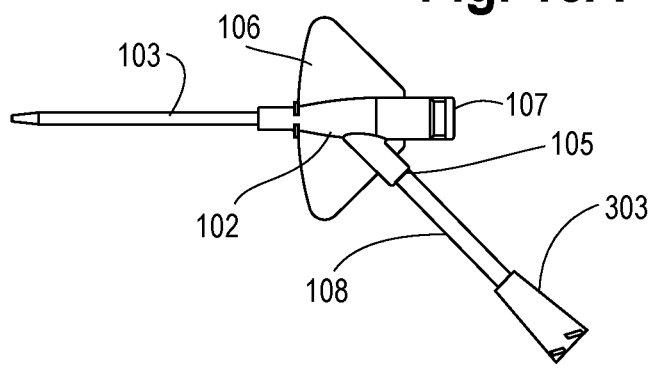
FIGS. 15A, 15B, and 15C illustrate three configurations of near access adapters for use in embodiments herein, including.
Figure 15B:
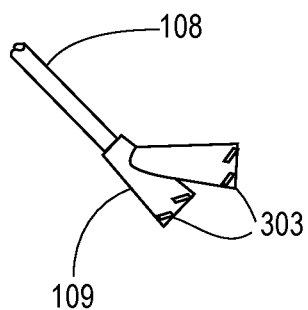
Figure 15C:
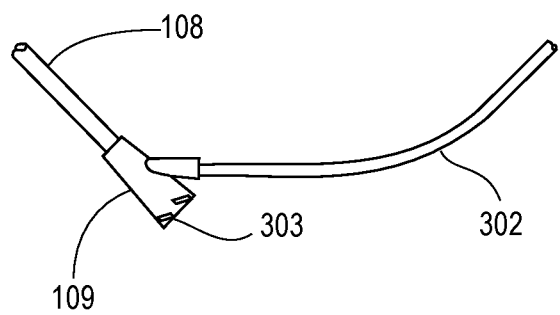

FIGS. 15A, 15B, and 15C accordingly illustrate three configurations of near access adapters for use in embodiments herein. As illustrated, FIG. 15A shows side port 105 connecting to extension tubing 108 configured with a single port near access adapter as a luer adapter 303. FIG. 15B shows extension tubing 108 configured with a dual port near access adapter as two luer adapters 303. FIG. 15C shows extension tubing 108 configured with a dual port near patient access adapter configured as a luer adapter 303 and secondary extension tubing 302.

Figure 16A:
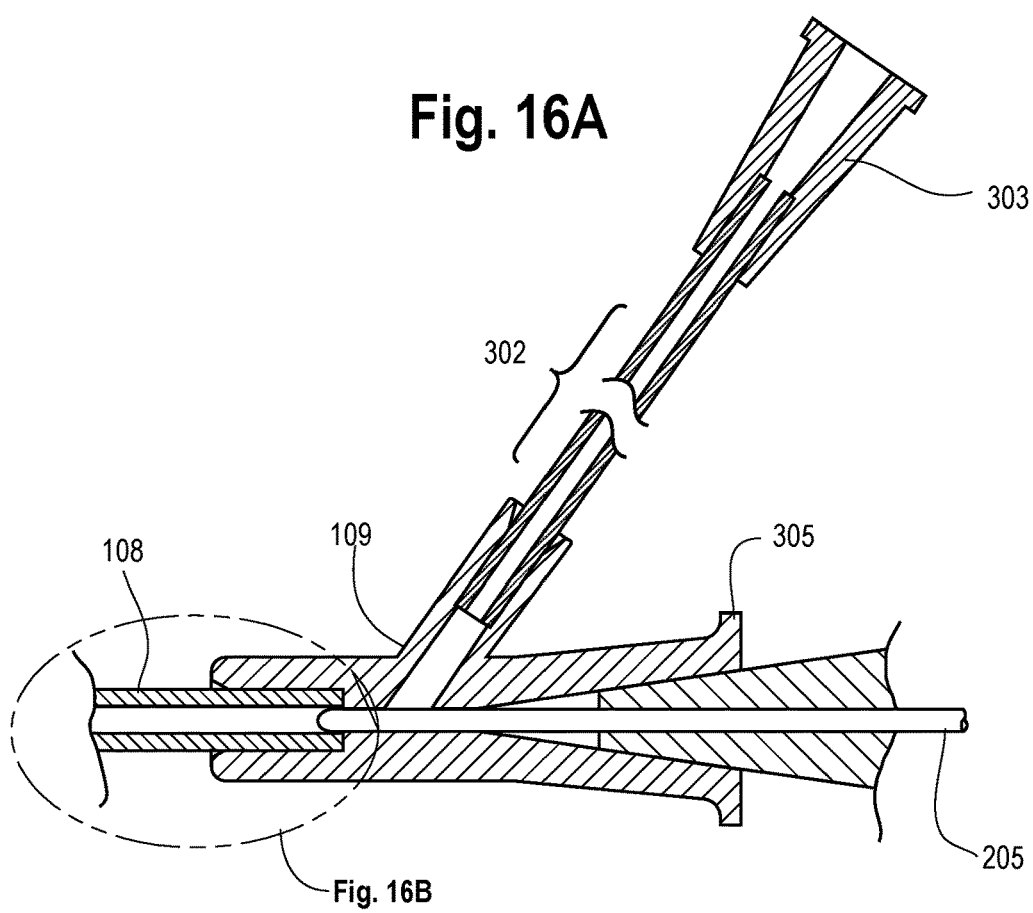
FIG. 16A illustrates another configuration of a near access adapter for insertion of a probe into the integrated catheter, according to some embodiments herein.
Figure 16B:
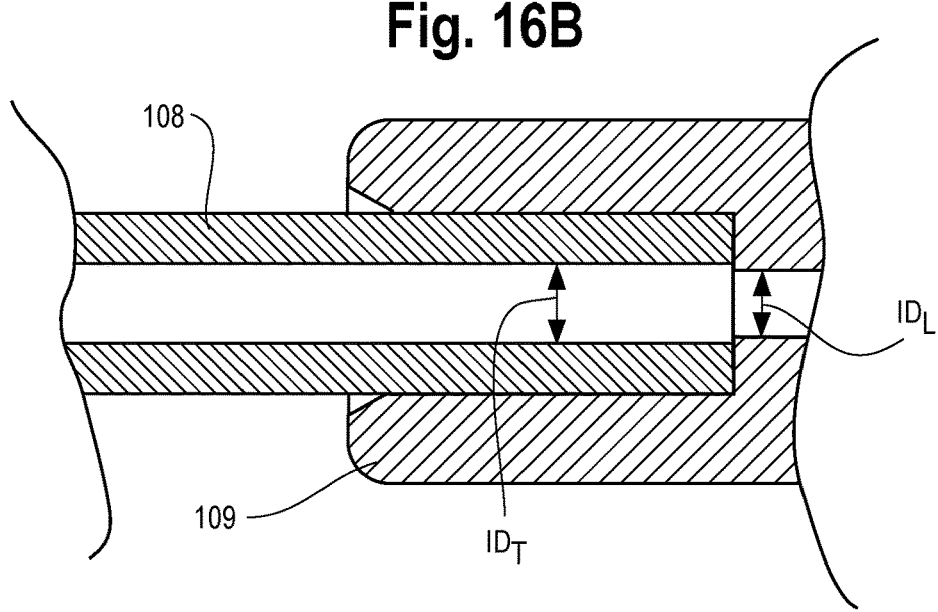
FIG. 16B is a detail view of the near access adapter of FIG. 16A.

FIG. 16A illustrates a detail view of a near access adapter for insertion of a probe into the vascular access device (e.g., integrated catheter), according to some embodiments herein. As shown, extension tubing 108 is configured with a dual port y-adapter 109 terminating in access adapter 305 for insertion of probe 205 and luer adapter 303 connected through secondary extension tubing 302. A conical fitting is also shown (not labelled) to the right of FIG. 16A, facilitating insertion of probe 205 into access adapter 305. As shown, the inner diameter of extension tubing 108 $ID_T$ is greater than the inner diameter of the lumen of y-adapter 109 $ID_L$, to facilitate passage of probe 205 through the system (FIG. 16B).

Figure 17A:
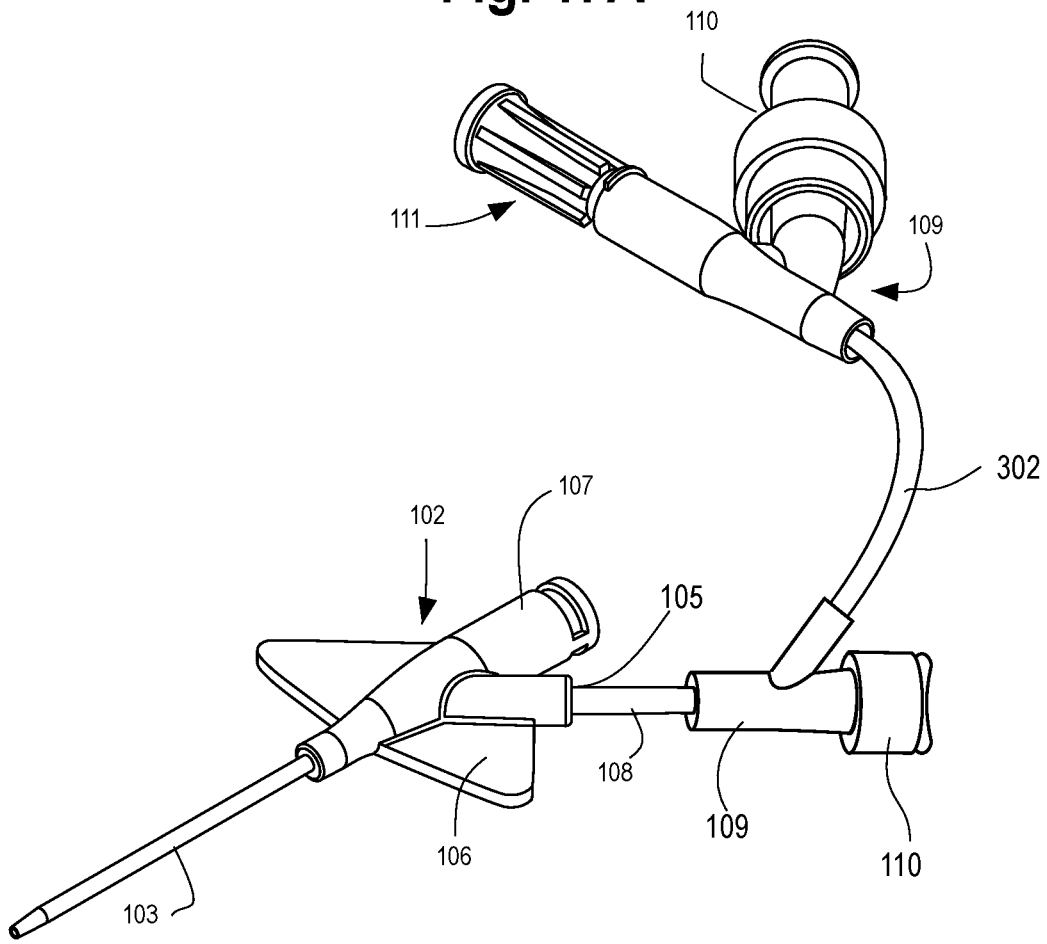
FIG. 17A illustrates another configuration of a near access adapter for insertion of a probe into an integrated catheter, according to some embodiments herein.
Figure 17B:
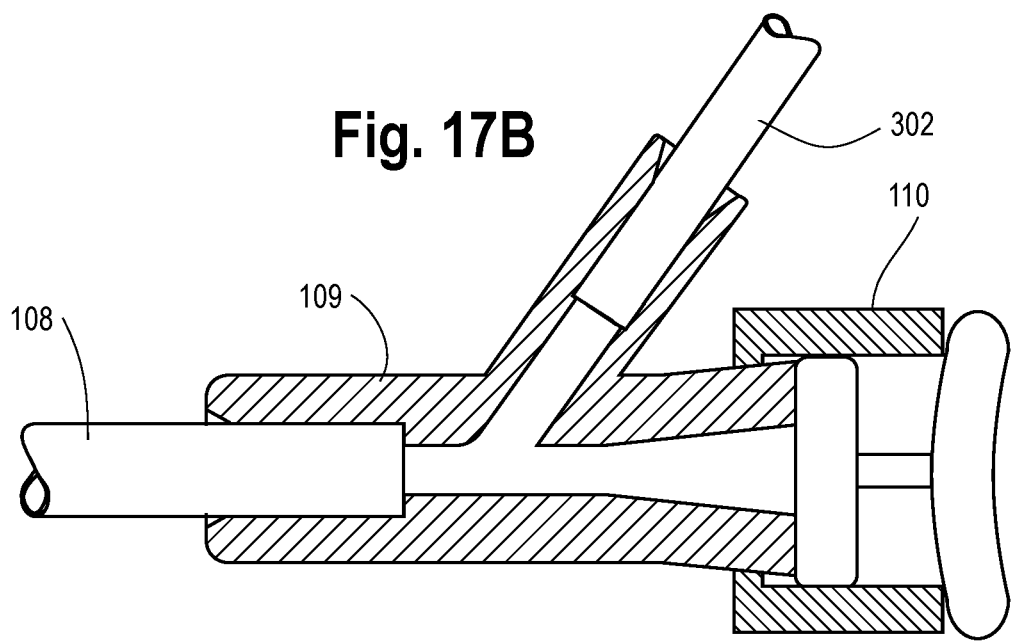
FIG. 17B is a detail view of the near access adapter of FIG. 17A.

FIG. 17A illustrates another configuration of a near access adapter for insertion of a probe into the vascular access device (e.g., integrated catheter). As shown, dual port y-adapter 109 terminates in a near access adapter, in this case configured as integrated Q-Syte™ needleless connector 110. Secondary extension tubing 302 leads to a separate dual port y-adapter 109 which terminates in a separate Q-Syte™ needleless connector 110 and air vent plug 111. In this embodiment, the proximity of the near access adapter to side port 105 is apparent, allowing a much shorter probe length than conventional designs. FIG. 17B illustrates a detail view of the near access adapter shown in FIG. 17A.

Figure 18:
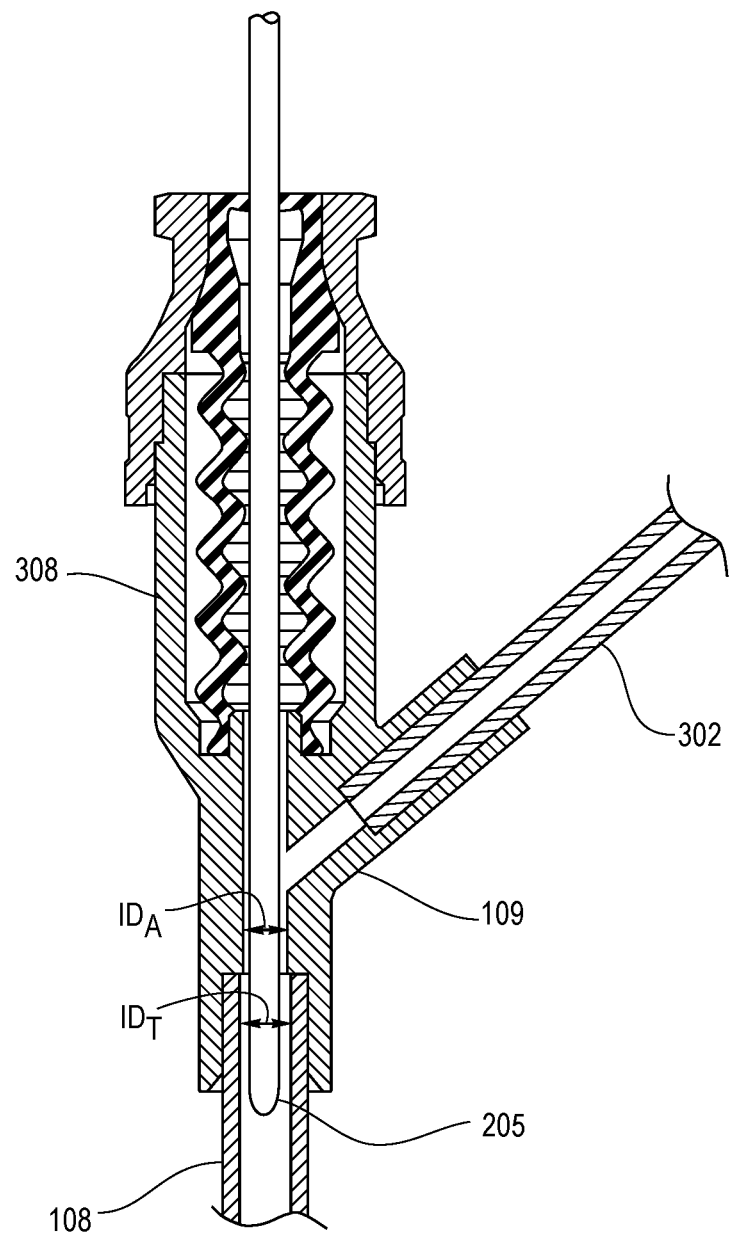
FIGS. 18 and 19 illustrate another configuration of a near access adapter for insertion of a probe into an integrated catheter, including an integrated SmartSite™ needleless connector.
Figure 19:
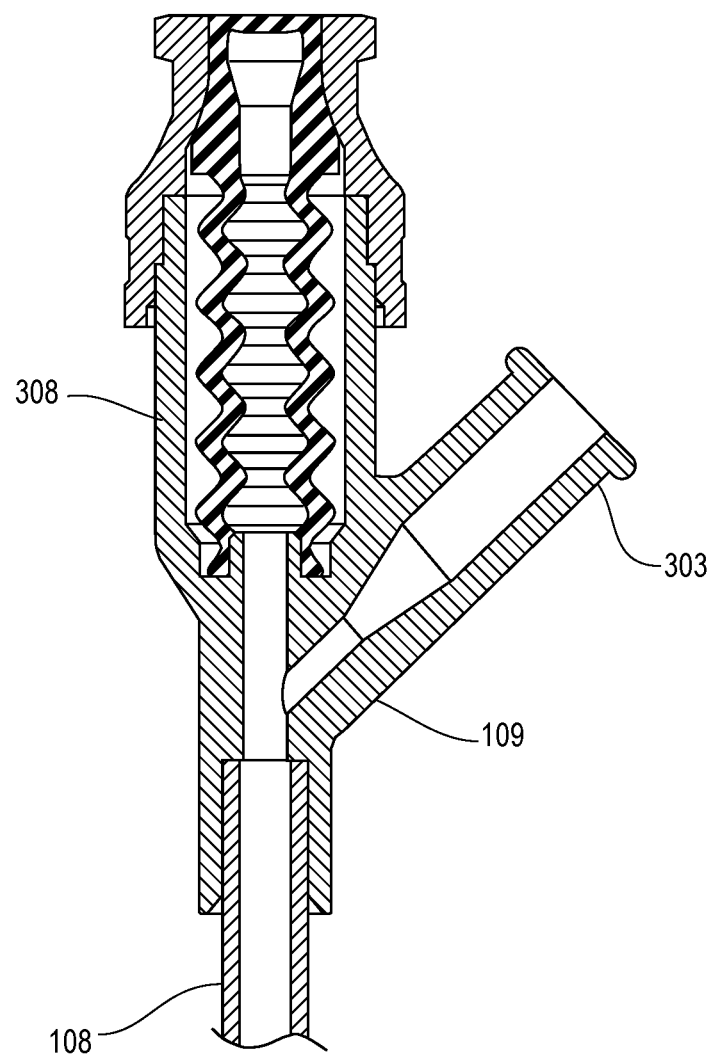

FIGS. 18 and 19 illustrate another configuration of a near access adapter for insertion of probe 205 into the vascular access device (e.g., integrated catheter). As shown, dual port y-adapter 109 terminates in an integrated SmartSite™ needleless connector 308, with a separate secondary extension tubing 302. In FIG. 18, probe 205 is shown advancing through integrated SmartSite™ needleless connector 308 into the system, with increasing internal diameter of downstream extension tubing 108.

Figure 20:
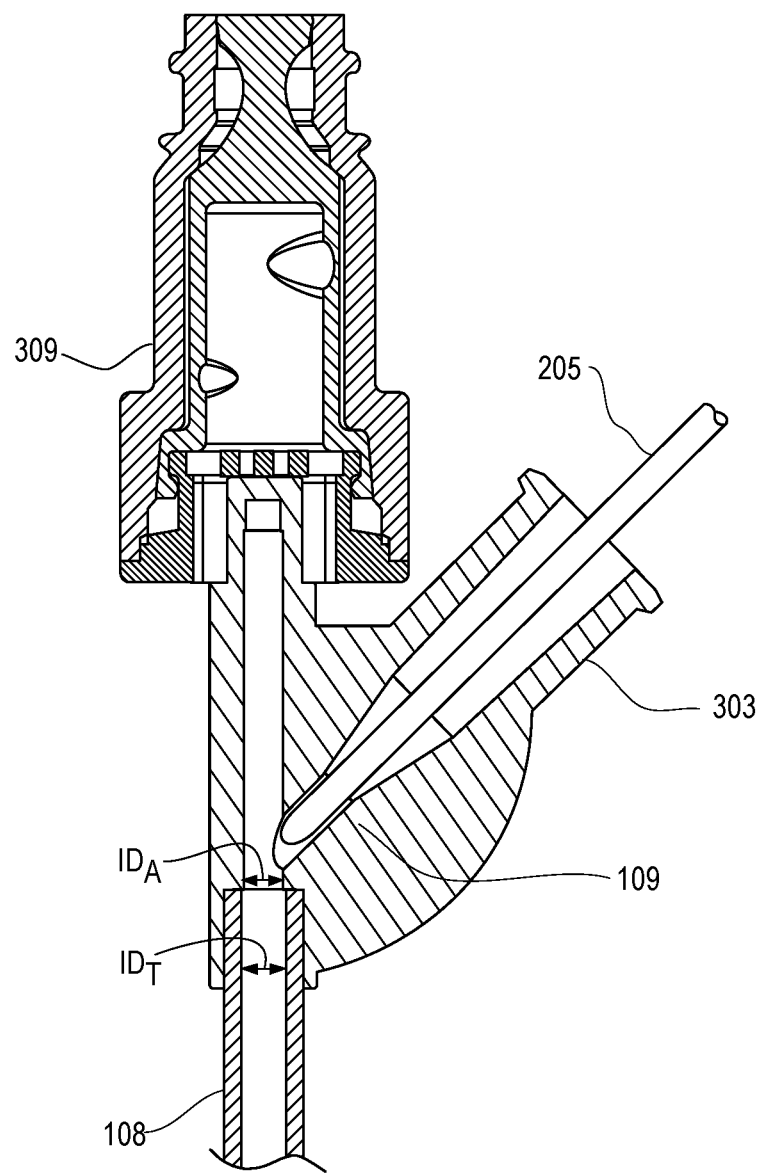
FIG. 20 illustrates another configuration of a near access adapter for insertion of a probe into an integrated catheter, including an integrated MaxZero™ needleless connector.

FIG. 20 illustrates another configuration of a near access adapter for insertion of probe 205 into a vascular access device (e.g., integrated catheter). As shown, dual port y-adapter 109 terminates in integrated MaxZero™ needleless connector 309, with a separate luer adapter 303 directly associated with y port adapter 109 (i.e., without secondary extension tubing). Probe 205 is shown advancing through luer adapter 303 into the system, with increasing internal diameter of downstream extension tubing 108. In this case, probe 205 cannot pass through MaxZero™ needleless connector 309 because the MaxZero™ does not have an opening or slit through which the probe could pass unobstructed into y-adapter 109 and extension tube 108. Therefore probe 205 must pass through luer adapter 303.

While some embodiments of vascular access devices herein are described for use with a removable needleless connector, in other embodiments and configurations, a non-removable needleless connectors may also be used.

Accordingly, various single or dual port near access adapters allow passage of a probe into the disclosed vascular access device (e.g., integrated catheter), with or without a separate luer adapter.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A vascular access device, comprising:
   a catheter for insertion into a biological site;
   a catheter adapter having a catheter hub and a side port coupled to the catheter hub, the catheter hub having a first end operably coupled to the catheter, a second end opposite the first end, and an internal wall defining an internal fluid passageway therebetween, the side port having another internal wall defining a lumen in fluid communication with the internal fluid passageway, wherein the other internal wall of the side port comprises a distal surface and a proximal surface opposite the distal surface, wherein the side port further comprises a protrusion extending outwardly from the proximal surface; and
   a septum disposed within the internal fluid passageway;
   wherein the protrusion is configured to deflect a probe entering the catheter hub from the side port towards the first end of the catheter hub such that the probe contacts the internal wall at a contact angle between 90 degrees and 180 degrees.

2. The vascular access device of claim 1, wherein the contact angle is between 90 degrees and 180 degrees along the length of the internal fluid passageway and to the first end.

3. The vascular access device of claim 1, wherein the contact angle is between 120 degrees and 180 degrees.

4. The vascular access device of claim 1 the protrusion extending into the lumen of the side port, the internal fluid passageway, and/or the extension tube.

5. The vascular access device of claim 4, wherein the catheter hub is configured to facilitate the probe entering from the side port at an entrance angle of less than 45 degrees.

6. The vascular access device of claim 1, further comprising a catheter wedge, the catheter wedge defining at least a portion of the internal wall.

7. The vascular access device of claim 1, further comprising an extension tube connected to and fluidly coupled with the side port.

8. The vascular access device of claim 1, further comprising an access adapter in fluid communication with the side port and permitting insertion of the probe into the catheter through the side port with or without a separate luer adapter.

9. The vascular access device of claim 8, wherein the access adapter is selected from the Group consisting of the luer adapter, a needle-less connector, a fluid control valve, and a non- luer proprietary access valve.

10. The integrated catheter of claim 1, wherein the entrance angle of the longitudinal axis of the side port is less than 45 degrees with respect to the major axis of the catheter hub.

11. The integrated catheter of claim 1, wherein the internal wall opposite the side port has a convex surface or a concave surface.

12. A method of using the vascular access device of claim 7, the method comprising: inserting the probe into the extension tube;
advancing the probe through the extension tube and into the side port;
advancing the probe from the side port through the internal fluid passageway and into the catheter; and
advancing the probe through the catheter and into peripheral vasculature of a subject.

13. The method of claim 12, wherein the probe maintains the contact angle with the internal wall of greater than 90 degrees and less than 180 degrees along the length of the internal fluid passageway.

14. The method of claim 12, wherein the probe is passed through an access adapter before being inserted into the extension tube, the access adapter in fluid communication with the extension tube and permitting insertion of the probe into the catheter through the side port with or without a separate luer adapter.

15. The vascular access device of claim 1, wherein the protrusion is proximate the internal fluid passageway.

16. An integrated catheter comprising:
a catheter for insertion into a biological site;
a catheter adapter having a catheter hub and a side port, the catheter hub having a first end operably coupled to the catheter, a second end opposite the first end, and an internal wall defining an internal fluid passageway therebetween, the side port having another internal wall defining a lumen in fluid communication with the internal fluid passageway, wherein the other internal wall of the side port comprises a distal surface and a proximal surface opposite the distal surface;
a septum disposed within the internal fluid passageway, wherein the septum comprises a protrusion extending past the proximal surface towards a central axis of the side port; and
the internal wall further defining a transition step between a larger diameter portion of the internal fluid passageway proximal to the second end and a smaller diameter portion of the internal fluid passageway at the first end;
wherein the septum is configured to deflect a probe entering the catheter hub from the side port such that the probe contacts the transition step at a contact angle between 90 degrees and 180 degrees.

17. The integrated catheter of claim 16, further comprising the probe at least partially disposed within the side port.

* * * * *